United States Patent [19]

Prill

[11] 4,440,562

[45] Apr. 3, 1984

[54] HERBICIDAL EMULSIONS

[75] Inventor: Erhard J. Prill, Kirkwood, Mo.

[73] Assignee: Monsanto Company, St. Louis, Mo.

[21] Appl. No.: 285,166

[22] Filed: Jul. 20, 1981

[51] Int. Cl.$^3$ ................. A01N 25/08; A01N 25/22
[52] U.S. Cl. ................................. 71/86; 71/118; 71/DIG. 1
[58] Field of Search ................ 71/86, DIG. 1, 118

[56] References Cited

U.S. PATENT DOCUMENTS

| | | | |
|---|---|---|---|
| 3,442,945 | 5/1969 | Olin | 71/118 |
| 3,547,620 | 12/1970 | Olin | 71/118 |
| 3,799,758 | 3/1974 | Franz | 71/86 |
| 3,853,530 | 12/1974 | Franz | 71/86 X |

*Primary Examiner*—Catherine L. Mills
*Attorney, Agent, or Firm*—Patricia A. Coburn; Richard H. Shear

[57] ABSTRACT

The invention is directed to a water-dispersible herbicide emulsion composition which contains as the active ingredient a water-soluble herbicide, i.e., the isopropylamine salt of N-phosphonomethylglycine, combined with a water-insoluble 2-haloacetanilide herbicide, as for example, 2-chloro-N-methoxymethyl-2',6'-diethyl acetanilide (alachlor).

8 Claims, No Drawings

HERBICIDAL EMULSIONS

BACKGROUND OF THE INVENTION

The present invention relates to liquid herbicidal emulsions containing as the active ingredient, the isopropylamine salt of N-phosphonomethylglycine, which is a water soluble herbicide in combination with a water-insoluble 2-haloacetanilide herbicide, preferably 2-chloro-N-methoxymethyl-2',6'-diethylacetanilide. The herbicidal emulsions described herein are advantageously employed to replace mechanical tillage in the preparation of a seedbed in no-tillage farming.

No-tillage refers to a wide variety of crop production systems using reduced or limited amounts of tillage. Various estimates indicates that by the year 2010 over 90% of the cropland in the United States will be planted using no-till methods. No-till farming is advantageous in that it saves water because there is less run-off, less direct evaporation losses and thus more water available for crop growth and higher yields. No-till reduces the number of field operations along with labor and machinery requirements with corresponding savings of fuel. In areas where double-cropping is practical, no-till enables the farmer to plant a second crop as the first crop is harvested. No-till also offers the opportunity to farm more extensively on, for example, sloping land where erosion is a problem if the crop is planted using conventional plowing. However, successful practice of no-till farming requires that the farmer rely almost completely on herbicides for weed control. The use of herbicides replaces mechanical tillage in the preparation of the seed bed. No-tillage usually requires a combination of a contact herbicide for quick burn-down of existing vegetation and use of one or more residual herbicides to provide season-long weed control. Because in the practice of no-tillage farming, the farmer almost totally relies upon agricultural chemicals for control of unwanted vegetation, proper preparation and application of the herbicides is critical. Generally speaking, in the practice of no-tillage farming, the herbicide is applied by spraying; thus, usage of correct spray nozzles, right sprayer speed, right amount of water or liquid nitrogen carrier, and, most importantly, proper mixing of the herbicides is highly important.

It is known in the art that a formulated composition containing, as the active ingredient, the isopropylamine salt of N-phosphonomethyl glycine which is sold under the tradename Roundup ®, may be tank-mixed with formulated 2-chloro-N-methoxymethyl-2',6'-diethylacetanilide (commonly known as alachlor and commercially available under the tradename Lasso ®).

The isopropylamine salt of N-phosphonomethyl glycine (also known as the IPA salt of glyphosate) is a superior post-emergent herbicide effective against a broad spectrum of weeds. 2-Haloacetanilide herbicides, on the other hand, are preferentially employed as pre-emergent herbicides and are especially effective in the control of the grass weeds. Tank-mixtures of commercially available formulations of these two types of herbicides, especially Roundup ® herbicide tank-mixed with Lasso ® herbicide, have proven very useful in no-till or minimum till farming.

In actual use, tank-mixtures suffer from the disadvantage that such mixtures require that the farmer must purchase and store two separate herbicides until actual preparation of the tank-mixture, which is an inconvenience. The farmer is also required to measure out varying amounts of the two different herbicides allowing for the possibility of mixing errors. Accordingly, a pre-packaged mixture containing both types of herbicides in one container is highly desirable since the farmer only has to purchase and store the pre-packaged mixture containing both of the active ingredients and the possibility of mixing errors is eliminated.

The herbicidal emulsions of the present invention provide flowable, herbicidal emulsion compositions in which a water-soluble herbicide, i.e., the isopropylamine salt of glyphosphate is combined with a water-insoluble 2-haloacetanilide herbicides, e.g., 2-chloro-N-methoxymethyl-2',6'-diethylacetanilide as a pre-packaged, one-container mixture which is conveniently stored, is storage-stable and easily dispersed in water and which can contain a high concentration of the herbicide active ingredients, e.g., up to and including about eight pounds herbicide per gallon of formulation.

SUMMARY OF THE INVENTION

The present invention is directed to a water-dispersible herbicide emulsion composition which contains as the active ingredient a water-soluble herbicide, i.e., the isopropylamine salt of N-phosphonomethylglycine, combined with a water-insoluble 2-haloacetanilide herbicide, as for example, 2-chloro-N-methoxymethyl-2',6'-diethyl acetanilide (alachlor) at a weight ratio of glyphosate salt to the 2-haloacetanilide herbicide of from 1:10 to 5:1.

The herbicidal emulsion compositions described herein are storage-stable and water-dispersible and can contain a high concentration of active ingredient, i.e., up to and including about six pounds herbicide per gallon of formulation.

DETAILED DESCRIPTION OF THE INVENTION

The flowable herbicidal emulsion compositions of the present invention comprise an aqueous phase which contains the water-soluble herbicide active ingredient, i.e., the isopropylamine salt of N-phosphonomethyl glycine in which is dispersed an oil or organic phase which contains the oil soluble (water-insoluble) herbicide active ingredient, the 2-haloacetanilide herbicide. The herbicidal emulsion formulation of the present invention consists essentially of the following components:

| | Ingredients | % By Weight |
|---|---|---|
| A. | Isopropyl amine salt of of N—phosphonomethylglycine | 6.0–35.0 |
| B. | Surfactant for Component A | 2.0–12.5 |
| C. | 2-Haloacetanilide herbicide | 5.0–60.0 |
| D. | Organophilic clay | 0–3.0 |
| E. | Emulsifier | 4.5–9.0 |
| F. | Organic solvent | 0–30.0 |
| G. | Water | balance |
| | | Total 100.0 |

The concentration of the isopropylamine salt of N-phosphonomethyl glycine present in the emulsion will range from about 6.0 to 35.0 percent by weight, preferably from about 10.0 to 25.0 percent by weight and most preferably at about 15.0 percent by weight of total composition.

The phrase "Surfactant for Component A" as used herein refers to surfactants which may suitably be employed with the isopropylamine salt of N-phosphonomethyl glycine and are of the type described in U.S. Pat. No. 3,799,758. Such surfactants include, but are not limited to, ethoxylated fatty amines, e.g., ethoxylated tallow amines, ethoxylated soyamines, ethoxylated cocoamines, ethoxylated tertiary octyl amines, ethoxylated ether amines and propoxylated/ethoxylated amines. Additionally, water soluble salts of alkyl sulfates have been found to be effective surfactants for use with the IPA salt of glyphosate as described in U.S. Ser. No. 254,312, filed Apr. 15, 1981, titled "Aqueous Herbicide And Plant Growth Regulator Formulation Having Low Temperature Storage Stability", Erhard J. Prill, inventor. Among the preferred surfactants for use herein are the ethoxylated fatty amines of the type described above. As would be recognized by one skilled in the art, various ethoxylated fatty amines are commercially available and are described in "McCutcheon's Detergents and Emulsifiers, North American Edition 1980 Annual", McCutcheon Division, MC Publishing Co., 175 Rock Rd., Glen Rock, N.J. 07452, USA.

The "surfactant for Component A" will be present in the emulsion composition at from about 2.0 to 12.5 percent by weight, preferably at about 5.0 to 7.5 percent by weight and most preferably at about 5.0 to 6.0 percent by weight of the emulsion composition.

2-Haloacetanilide herbicides which are contemplated for use herein are oil-soluble, i.e., they are soluble in organic solvents or else are oily liquids at room temperature, in which case the 2-haloacetanilide herbicide will itself be the organic phase liquid and use of an organic solvent in the composition will not be required. Such 2-haloacetanilide herbicides are described in U.S. Pat. No. 3,442,945, U.S. Pat. No. 3,547,620 and U.S. Pat. No. 3,952,056.

Exemplary of the specific 2-haloacetanilides which may be usefully employed in the emulsion compositions of this invention include, but are not limited to the following: 2-chloro-2',6'-diethyl-N-(methoxymethyl)acetanilide, (commonly known as alachlor), N-isopropyl-2-chloroacetanilide, (commonly known as propachlor), N-(butoxymethyl)-2',6'-diethyl-2-chloroacetanilide, (commonly known as butachlor), α-chloro-2'-ethyl-6'-methyl-N-(1-methyl-2-methoxymethyl)acetanilide (commonly known as metolachlor) and 2-chloro-2'-ethyl-o-acetotoluidine. Preferred for use herein is alachlor, i.e., 2-chloro-2',6'-diethyl-N-(methoxymethyl)acetanilide. The herbicidal 2-haloacetanilide active ingredient will be present in the emulsion composition at a concentration of from about 5.0 to about 60.0 percent by weight, preferably at from about 20.0 to 35.0 percent by weight and most preferably at about 26.0 to 28.0 percent by weight.

Any organophilic clay which swells in the presence of an organic solvent may be used in the emulsions described herein. The organophilic clay should have high gelling efficiency over a wide range of intermediate and low polarity organic liquids and should be capable of reproducible thioxotropic consistency over a wide temperature range. The organophilic clay provides increased viscosity and is a specific gravity modifier of the dispersed phase. Exemplary of such an organophilic clay is Bentone ® 34 manufactured by NL Industries, Inc., Industrial Chemicals Division, P.O. Box 700, Highstown, N.J. 08520. The organophilic clay may be present in the emulsion compositions described herein at a concentration of from about zero to about 3.0 percent by weight, preferably at from about 1.25 to about 1.75 percent by weight.

Emulsifiers found to be useful in the preparation of the herbicidal emulsions described herein are alkyl aryl sulfonates which are anionic surfactants, phosphate esters of nonyl phenol ethoxylates which are non-ionic surfactants and polyalkylene glycol ethers, which are nonionic surfactants. Exemplary of the alkyl aryl sulfonate surfactants are, for example Arnnate ® 460 and Arnnate ® 462 manufactured by Arjay, Inc., P.O. Box 45045, Houston, Tex. 77045. Exemplary of the phosphate esters of nonyl phenol ethoxylate surfactants are, for example, Flo Mo ® 4 to 30 NP, tradenames of phosphate esters of nonyl phenol ethoxylates manufactured by Sellers Chemical Corporation, 1320 Sams Avenue, P.O. Box 23523, Harahans, LA 70183. Exemplary of the polyalkylene glycol ethers are Tergitol ® XH and Tergitol ® XD manufactured by Union Carbide Corporation, Chemicals and Plastics, 270 Park Ave., New York, N.Y. 10017. The emulsifier is present in the emulsion composition at a concentration of from about 4.5 to about 9.0 percent by weight, preferably at about 4.0 to 6.0 percent by weight.

Any organic solvent in which the 2-haloacetanilide herbicide is soluble and which is non-reactive to said herbicide and which is essentially water-insoluble may be employed in the emulsions described herein. Suitable organic solvents which are contemplated for use herein are, for example, monochlorobenzene, xylene, kerosene, $C_9$ aromatics, and the like. As is readily recognized by one skilled in the art, organic solvents which have a low flash point and/or which are of low toxicity to man will be preferably utilized in the emulsion compositions described herein. The organic solvent is present in the emulsion composition at a concentration of from 0 to about 30.0 percent by weight, preferably at from about 10.0 to about 20.0 percent by weight.

In the emulsions of the present invention, water is present in varying amounts, depending upon the quantities employed of the other ingredients and is present in sufficient quantity to serve as the continuous phase for the water-insoluble dispersed herbicide component.

Minor quantities, i.e., from about 0.5 to about 5.0 percent by weight of one or more inert formulation adjuvants, such as anti-foaming agent, anti-caking agents, biocides, dyes, anti-corrosion agents, freeze-point depressants and the like may be incorporated into the herbicide emulsion compositions of the present invention, especially if said compositions are to be stored for any extended period of time prior to use, particularly under adverse storage conditions.

Preparation of the emulsion compositions described herein may be carried out at ambient temperature, no application of heat or undue pressure normally being need to obtain the desired homogeneous, flowable emulsion. However, it has been found that the order of addition of the components of the emulsion compositions described herein will affect the quality, i.e., homogeneity, dispersibility, etc. Accordingly, the herbicidal emulsions described herein are preferentially prepared according to the following steps:

1. The organophilic clay is blended, using agitation, with the organic solvent and a portion of the 2-haloacetanilide herbicide component, usually about one-fourth of the 2-haloacetanilide herbicide is suitable and agitation is continued until a homogeneous mix is obtained;

2. The mixture of Step 1 is subjected to high shear using an appropriate shearing means;

3. The remaining ingredients are added to the viscous mix of Step 2, preferably in the following order: remaining 2-haloacetanilide herbicide, emulsifier, isopropylamine salt of glyphosate, surfactant for IPA salt of glyphosate and water; and 4. The resulting emulsion is homogenized using a shearing means.

Agitation, homogenization and dispersion of the dispersed or organic phase into the continuous or aqueous phase may be accomplished using shearing means known to those in the art to be capable of producing sufficient shear to produce dispersion, emulsification and/or homogenization. Illustrative of such shearing means is the "Polytron" homogenizer, sold by Brinkmann Instruments, Inc., Cantiague Rd., Westbury, N.Y. 11590, utilizes mechanical shearing with sonic energy to effect homogenization, dispersion or emulsification and the Tekmar, "Display Reactor DR 3-916" available from the Tekmar Company, P.O. Box 372021, Cincinnati, Ohio 45222.

The following examples are illustrative of the herbicidal emulsions contemplated by the present invention. Unless otherwise indicated, all examples were prepared according to the procedure described in Example 1.

EXAMPLE 1

The emulsion composition described in this example was prepared as follows. Bentone ® 34, an organically modified montmorillonite clay which swells in the presence of an organic solvent, was blended with agitation with all of the monochlorobenzene (MCB) and about one-fourth of the alachlor herbicide. Agitation was continued until a homogeneous mix was obtained, about 15 minutes. MCB partially swelled the clay, giving a product which was too viscous to handle; therefore, one-fourth of the alachlor in the formulation was used as a diluent. It was found that if appreciably more alachlor was used, swelling was less complete during the shearing step.

The mixture was then subjected to high shear by two passes through a Tekmar with three super-fine generators. The rest of the alachlor and the emulsifier, Flo Mo ® 6NP, were added next and the mixture was agitated for about 15 minutes to completely dissolve the viscous emulsifier. Finally, the aqueous components, i.e., isopropylamine salt of N-phosphonomethyl glycine, surfactant for said herbicide and water, were added with continued agitation. The resulting emulsion was homogenized by one pass through a Tekmar with three super-fine generators.

| | Ingredients | % By Weight |
|---|---|---|
| A. | N—phosphonomethylglycine, isopropyl amine salt (62%) | 24.20 |
| B. | Surfactant for Component A | 5.58 |
| C. | Alachlor technical (90%) | 29.96 |
| D. | Monochlorobenzene | 16.48 |
| E. | Bentone ® 34 | 1.56 |
| F. | Flo Mo ® 6NP | 5.50 |
| G. | Water | 16.72 |
| | Total | 100.00 |

EXAMPLE 2

| | Ingredients | % By Weight |
|---|---|---|
| A. | N—phosphonomethylglycine, isopropyl amine salt (62%) | 34.18 |
| B. | Surfactant for Component A | 7.88 |
| C. | 2-Chloro-2'-ethyl-o-acetotoluidine[1] | 30.28 |
| D. | Bentone ® 34 | 1.22 |
| E. | Emulsifier | |
| | Tergitol ® XH | 6.00 |
| | Arnnate ® 462 | 1.85 |
| F. | Butyrolactone[2] | 0.58 |
| G. | Water | 18.01 |
| | Total | 100.00 |

EXAMPLE 3

| | Ingredients | % By Weight |
|---|---|---|
| A. | N—phosphonomethylglycine, isopropyl amine salt (62%) | 23.88 |
| B. | Surfactant for Component A | 5.50 |
| C. | Alachlor technical (93%) | 29.65 |
| D. | Bentone ® 34 | 1.56 |
| E. | Flo Mo ® 6NP | 5.50 |
| F. | Monochlorobenzene | 16.16 |
| G. | Water | 17.75 |
| | Total | 100.00 |

EXAMPLE 4

| | Ingredients | % By Weight |
|---|---|---|
| A. | N—phosphonomethylglycine, isopropyl amine salt (62%) | 27.24 |
| B. | Surfactant for Component A | 6.28 |
| C. | Alachlor technical (91%) | 30.20 |
| D. | Bentone ® 34 | 1.43 |
| E. | Flo Mo ® 6NP | 5.50 |
| F. | Organic Solvent | |
| | Monchlorobenzene | 15.34 |
| | Xylene | 6.34 |
| G | Water | 7.67 |
| | Total | 100.00 |

EXAMPLE 5

| | Ingredients | % By Weight |
|---|---|---|
| A. | N—phosphonomethylglycine, isopropyl amine salt (62%) | 17.93 |
| B. | Surfactant for Component A | 4.14 |
| C. | Butachlor (92%) | 48.35 |
| D. | Flo Mo ® 6NP | 5.50 |
| E. | Water | 24.08 |
| | Total | 100.00 |

EXAMPLE 6

| | Ingredients | % By Weight |
|---|---|---|
| A. | N—phosphonomethylglycine, isopropyl amine salt (62%) | 27.30 |
| B. | Surfactant for Component A | 6.30 |
| C. | Alachlor technical (93%) | 30.20 |
| D. | Bentone ® 34 | 1.40 |
| E. | Flo Mo ® 6NP | 5.50 |
| F. | Xylene | 20.93 |
| G. | Butyrolactone | 0.68 |

| Ingredients | % By Weight |
|---|---|
| G. Water | 7.69 |
| Total | 100.00 |

One-third of the alachlor was mixed with the xylene, Bentone ® 34 and butyrolactone and sheared as in Example 1.

EXAMPLE 7

| Ingredients | % By Weight |
|---|---|
| A. N—phosphonomethylglycine, iso-propyl amine salt (62%) | 18.66 |
| B. Surfactant for Component A | 4.30 |
| C. Butachlor Technical (92%) | 50.28 |
| D. Flo Mo ® 6NP | 5.50 |
| E. Kerosene | 16.00 |
| F. Water | 5.26 |
| Total | 100.00 |

EXAMPLE 8

| Ingredients | % By Weight |
|---|---|
| A. N—phosphonomethylglycine, iso-propyl amine salt (62%) | 43.33 |
| B. Surfactant for Component A | 9.99 |
| C. Alachlor technical (93%) | 5.78 |
| D. Bentone ® 34 | 0.48 |
| E. Flo Mo ® 6NP | 5.50 |
| F. Monchlorobenzene | 5.04 |
| G. Water | 29.88 |
| Total | 100.00 |

One-half of the alachlor, monochlorobenzene and organophilic clay were subjected to high shear using a Polytron, which enhanced the swelling of the clay and greatly increased the viscosity of the dispersed (organic phase).

EXAMPLE 9

| Ingredients | % By Weight |
|---|---|
| A. N—phosphonomethylglycine, iso-propyl amine salt (62%) | 43.33 |
| B. Surfactant for Component A | 9.99 |
| C. Alachlor technical (93%) | 5.78 |
| D. Bentone ® 34 | 0.48 |
| E. Flo Mo ® 6NP | 5.50 |
| F. Monochlorobenzene | 27.72 |
| G. Water | 7.20 |
| Total | 100.00 |

All of the alachlor and 12 parts of the monochlorobenzene and the Bentone ® 34 were sheared as in Example 1.

EXAMPLE 10

| Ingredients | % By Weight |
|---|---|
| A. N—phosphonomethylglycine, iso-propyl amine salt (62%) | 27.02 |
| B. Surfactant for Component A | 6.23 |
| C. Alachlor technical (93%) | 6.00 |
| D. Bentone ® 34 | 0.28 |
| E. Flo Mo ® 6NP | 5.50 |
| F. Monchlorobenzene | 2.98 |
| G. Water | 51.99 |

| Ingredients | % By Weight |
|---|---|
| Total | 100.00 |

One-fourth of alachlor plus the monochlorobenzene and Bentone ® 34 were sheared as in Example 1.

EXAMPLE 11

| Ingredients | % By Weight |
|---|---|
| A. N—phosphonomethylglycine, iso-propyl amine salt (62%) | 9.25 |
| B. Surfactant for Component A | 2.13 |
| C. Alachlor technical (93%) | 18.50 |
| D. Bentone ® 34 | 1.35 |
| E. Flo Mo ® 6NP | 5.50 |
| F. Monochlorobenzene | 14.18 |
| G. Water | 49.09 |
| Total | 100.00 |

EXAMPLE 12

| Ingredients | % By Weight |
|---|---|
| A. N—phosphonomethylglycine, iso-propyl amine salt (62%) | 18.66 |
| B. Surfactant for Component A | 4.30 |
| C. Butachlor technical (93%) | 62.85 |
| D. Flo Mo ® 6NP | 6.00 |
| E. Kerosene | 2.94 |
| F. Water | 5.25 |
| Total | 100.00 |

The emulsions of this invention provides to one skilled in the art an easily flowable herbicide formulation which contains as the active ingredient a combination of water-soluble and oil-soluble herbicides. This composition has excellent bloom characteristics, i.e., it easily disperses when added to water. It can be diluted with water in all proportions to provide agglomerate-free, sprayable herbicide compositions of any desired herbicide concentration. Preparation of the spray formulation may be easily accomplished at the application site by simply ouring an appropriate amount of the emulsion composition in undiluted form, utilizing new or specialized spray techniques.

The sprayable, agglomerate-free herbicide composition formulated from the emulsion concentrate from this invention may be applied from all types of presently used equipment with no plugging of the spray nozzle or other malfunction of the spray equipment.

The herbicidal emulsions described herein produce weed control comparable to the conventional tank mixes of the active herbicidal ingredient. When the emulsion of Example 4 was compared with a comparable tank mix containing 1.6 pounds per gallon of the isopropylamine salt of glyphosate and 3.0 pounds per gallon of alachlor as the active ingredients, no significant differences in weed control were observed. The test procedures and test results are shown in Examples 9 and 10 and Tables I and II, respectively.

EXAMPLE 13

Triplicate pots were planted with green foxtail and barnyardgrass and covered with Ray slit loam soil prior to treatment. All materials were applied with a belt sprayer calibrated to apply 20 gallons of spray solutin per acre at 30 psi. All pots received ¼ inch overhead irrigation after treatment to activate the herbicides. Visual estimates of percent inhibition were made 2 weeks after treatment. The pots were then allowed to dry out and were then reseeded, recovered with the same soil, and allowed to grow for 15 days at which time visual estimates of inhibitions were again recorded. The results are summarized in Table I.

TABLE I

| Active Ingredients | Application Rate of Active Ingredients Lb/Acre | % Inhibition 2 WAT | | % Inhibition 4 WAT | |
|---|---|---|---|---|---|
| | | Foxtail | Barnyard-grass | Foxtail | Barnyard-grass |
| Isopropylamine salt of glyphosate/alachlor (1.6:3.0) tank mixed | 0.048 | 98 | 95 | 30 | 30 |
| | 0.024 | 98 | 70 | 10 | 20 |
| | 0.012 | 90 | 60 | — | — |
| Isopropylamine salt of glyphosate/alachlor (1.4:2.6) prepared according to Example 1 | 0.048 | 99 | 98 | 20 | 20 |
| | 0.024 | 99 | 80 | 10 | 20 |
| | 0.012 | 95 | 65 | — | — |

WAT = Weeks after treatment

EXAMPLE 14

Triplicate pans containing johnsongrass, Canada thistle, and quackgrass were sprayed with the treatments shown in Table II. The materials were applied using a belt sprayer calibrated to apply 20 gallons of spray solution per acre at 30 psi. Visual estimates of percent inhibition were made at 2 and 4 weeks after treatment (WAT). The results are summarized in Table II.

TABLE II

| Active Ingredients | Rate Lb/Acre | % Inhibition JG | | CT | | QG | |
|---|---|---|---|---|---|---|---|
| | | 2 WAT* | 4 WAT | 2 WAT | 4 WAT | 2 WAT | 4 WAT |
| Isopropylamine salt of glyphosate/alachlor (1.6:3.0) tank mixed | 0.77 | 75 | 85 | 85 | 85 | 90 | 95 |
| | 0.38 | 40 | 30 | 60 | 75 | 60 | 65 |
| | 0.195 | 10 | 10 | 10 | 10 | 10 | 5 |
| Isopropylamine salt of glyphosate/alachlor (1.4:2.6) emulsion prepared according to Example 1 | 0.77 | 75 | 50 | 80 | 80 | 85 | 85 |
| | 0.38 | 55 | 30 | 40 | 30 | 50 | 50 |
| | 0.195 | 0 | 0 | 0 | 0 | 0 | 5 |

*JG = Johnsongrass
CT = Canada Thistle
QG = Quackgrass
**WAT = Weeks after treatment It is to be understood that although the invention has been described with specific references to particular embodiments thereof, it is not to be so limited, since changes and alterations therein may be made which are within the full intended scope of this invention as defined by the appended claims.

I claim:

1. A herbicidal emulsion composition consisting essentially of the following components:
    A. from about 10.0 to about 25.0 percent by weight of the isopropylamine salt of N-phosphonomethylglycine;
    B. from about 2.0 to about 12.5 percent by weight of a surfactant for Component A;
    C. from about 20.0 to about 35.0 percent by weight of 2-chloro-2',6'-diethyl-N-(methoxymethyl) acetanilide;
    D. From about 1.25 to about 1.75 percent by weight of an organophilic clay;
    E. from about 4.5 to about 9.0 percent by weight of an emulsifier selected from the group consisting of alkyl aryl sulfonates, phosphate esters of nonyl phenol ethoxylates and polyalkyleneglycol ethers;
    F. from about 10.0 to about 20.0 percent by weight of an organic solvent in which 2-chloro-2',6'-diethyl-N-(methoxymethyl)acetanilide herbicide is soluble, which is nonreactive to said herbicide and which is essentially water-insoluble; and
    G. balance being made up of water.

2. An emulsion composition according to claim 1 wherein said organic solvent is monochlorobenzene.

3. A herbicidal emulsion composition consisting essentially of the following components:
    A. from about 10.0 to about 25.0 percent by weight of the isopropylamine salt of N-phosphonomethylglycine;
    B. from about 5.0 to about 7.5 percent by weight of a surfactant for Component A;
    C. from about 20.0 to about 35.0 percent by weight of 2-chloro-2',6'-diethyl-N-(methoxymethyl)acetanilide;
    D. from about 1.25 to about 1.75 percent by weight of an organophilic clay;
    E. from about 4.0 to about 6.0 percent by weight of an emulsifier selected from the group consisting of alkyl aryl sulfonates, phosphate esters of nonyl phenol ethoxylates and polyalkyleneglycol ethers;
    F. from about 10.0 to about 20.0 percent by weight of an organic solvent in which 2-chloro-2',6'-diethyl-N-(methoxymethyl)acetanilide herbicide is soluble, which is nonreactive to said herbicide and which is essentially water-insoluble; and
    G. balance being made up of water.

4. An emulsion composition according to claim 3 wherein said organic solvent is monochlorobenzene.

5. A herbicidal emulsion composition consisting essentially of the following components:
    A. about 15.0 percent by weight of the isopropylamine salt of N-phosphonomethylglycine;

B. about 5.0 to about 6.0 percent by weight of a surfactant for Component A;
C. about 26.0 to about 28.0 percent by weight of alachlor;
D. about 1.25 to about 1.75 percent by weight of an organophilic clay;
E. about 4.0 to about 6.0 percent by weight of phosphate ester of nonyl phenol ethoxylate emulsifier;
F. about 10.0 to about 20.0 percent by weight of monochlorobenzene; and
G. balance being made up of water.

6. An emulsion composition according to claim 5 containing from about 0.5 to about 5.0 percent of inert formulation adjuvants.

7. An emulsion composition according to claim 1 containing from about 0.5 to about 5.0 percent of inert formulation adjuvants.

8. An emulsion composition according to claim 3 containing from about 0.5 to about 5.0 percent of inert formulation adjuvants.

* * * * *

UNITED STATES PATENT AND TRADEMARK OFFICE
CERTIFICATE OF CORRECTION

PATENT NO. : 4,440,562  
DATED : April 3, 1984  
INVENTOR(S) : Erhard J. Prill

Page 1 of 2

It is certified that error appears in the above-identified patent and that said Letters Patent are hereby corrected as shown below:

Column 2, line 12: "herbicides," should be --herbicide,--

Column 6, Example 2: after "Total 100.00" insert

--$^{1}$In this example it was unnecessary to use an organic solvent since the 2-haloacetanilide herbicide is an oil at room temperature.

$^{2}$Butyrolactone was added to aid the organophilic clay as a pre-swelling agent.--

Column 8, Example 13, line 66: "slit" should be --silt--.

UNITED STATES PATENT AND TRADEMARK OFFICE
CERTIFICATE OF CORRECTION

PATENT NO. : 4,440,562

DATED : April 3, 1984

INVENTOR(S) : Erhard J. Prill

It is certified that error appears in the above-identified patent and that said Letters Patent is hereby corrected as shown below:

Example 4, line 41: "monchlorobenzene" should be --monochlorobenzene"

Example 8, line 32: "monchlorobenzene" should be --monochlorobenzene"

Example 10, line 67: "monchlorobenzene" should be --monochlorobenzene"

Column 8, line 45: "ouring" should be --pouring--

Column 8, Example 13, line 68: "solutin" should be --solution--

Column 9, Claim 1, line 65: "From" should be --from--

Signed and Sealed this

Fourteenth Day of May 1985

[SEAL]

Attest:

DONALD J. QUIGG

Attesting Officer  Acting Commissioner of Patents and Trademarks